United States Patent [19]

Kathawala

[11] 4,098,908

[45] * Jul. 4, 1978

[54] PHENOXYPHENYL PYRIDYL KETONES AND DERIVATIVES AND THEIR USE AS HYPOLEPIDEMIC AGENTS

[75] Inventor: Faizulla G. Kathawala, West Orange, N.J.

[73] Assignee: Sandoz, Inc., E. Hanover, N.J.

[ * ] Notice: The portion of the term of this patent subsequent to Mar. 8, 1994, has been disclaimed.

[21] Appl. No.: 700,161

[22] Filed: Jun. 28, 1976

Related U.S. Application Data

[63] Continuation-in-part of Ser. No. 623,754, Oct. 20, 1975, abandoned, which is a continuation-in-part of Ser. No. 573,856, May 2, 1975, abandoned, which is a continuation-in-part of Ser. No. 553,997, Feb. 28, 1975, abandoned.

[51] Int. Cl.$^2$ .................... C07D 213/50; A61K 31/44
[52] U.S. Cl. ................................. 424/263; 260/297 R
[58] Field of Search ..................... 260/297 R; 424/263

[56] References Cited

U.S. PATENT DOCUMENTS

| 3,426,036 | 2/1969  | Biel et al. ......................... 260/297 R |
| 3,506,720 | 4/1970  | Model et al. ...................... 260/613     |
| 3,852,455 | 12/1974 | Carr ................................. 424/267  |
| 3,891,661 | 6/1975  | Sugisaka et al. ................. 260/297 R     |

OTHER PUBLICATIONS

Sam et al., Journal of Pharmaceutical Sciences, vol. 60, pp. 936 to 939 (1971).

*Primary Examiner*—Alan L. Rotman
*Attorney, Agent, or Firm*—Gerald D. Sharkin; Richard E. Vila; Frederick H. Weinfeldt

[57] ABSTRACT

Phenoxyphenyl pyridyl carbinols and ketones, e.g., p-phenoxyphenyl-nicotinyl ketone, are useful as pharmaceutical agents. The ketones are obtainable by oxidation of corresponding phenoxyphenyl pyridyl carbinols.

27 Claims, No Drawings

PHENOXYPHENYL PYRIDYL KETONES AND DERIVATIVES AND THEIR USE AS HYPOLEPIDEMIC AGENTS

This is a continuation-in-part of copending application Ser. No. 623,754 (filed Oct. 20, 1975); now abandoned whch in turn is a continuation-in-part of then copending application Ser. No. 573,856 (filed May 2, 1975; now abandoned) which in turn is a continuation-in-part of then copending application Ser. No. 553,997 (filed Feb. 28, 1975; now abandoned).

This invention relates to organic compounds, and more particularly to phenoxyphenyl pyridyl carbinols and ketones, (and pharmaceutically acceptable acid addition salts thereof) and to pharmaceutical compositions containing such compounds, as well as to use of such compounds as pharmaceuticals.

The compounds of this invention are conveniently represented by the formula (I):

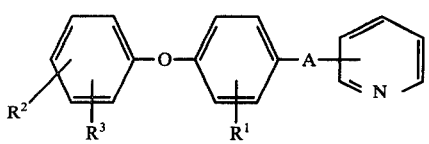

wherein each of $R^1$, $R^2$ and $R^3$ is, independently, a hydrogen atom, alkyl having from 1 to 4 carbons, or fluoro or chloro, i.e., a halogen atom having an atomic weight of from about 19 to 35; or each of $R^2$ and $R^3$ is, independently, alkoxy having from 1 to 4 carbons; provided that when $R^2$ and $R^3$ are on adjacent carbons they are not both branched alkyl or branched alkoxy, and

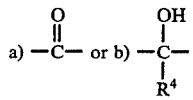

wherein $R^4$ is a hydrogen atom or alkyl having from 1 to 4 carbon atoms.

In the above-presented definitions of alkyl and alkoxy groups suitable as $R^1$, $R^2$, $R^3$ or $R^4$, it is to be understood that the alkyl portions may be methyl, ethyl, propyl or butyl, including isomers where such exist, e.g., t-butyl.

Compounds I, then consists of two classes of compounds, i.e., compounds Ia when A is of type a), i.e., carbonyl, and compounds Ib when A is of type b), i.e., a carbinol function.

Compounds Ia may be obtained by oxidizing (process a) in a suitable medium, a corresponding pyridyl carbinol (a compound Ib in which $R^4$ is a hydrogen atom), i.e., a compound Ib':

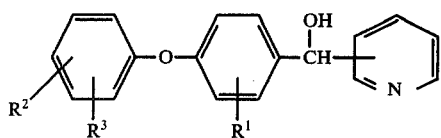

wherein $R^1$, $R^2$ and $R^3$ are as defined above.

The oxidation of a compound Ib', (process a) may be accomplished in the conventional manner for oxidizing a secondary aliphatic alcohol function to a carbonyl function, e.g., by reacting a compound Ib', at a temperature of, e.g., from about 20° to 140° C., in the presence of activated manganese dioxide ($MnO_2$) in a suitable medium, i.e., an inert solvent such as dichloromethane, 1,2-dichloroethane, benzene, toluene, xylene or dioxane. Preferably the reaction is carried out at the reflux temperature of the solvent, which is preferably dichloromethane, i.e., $CH_2Cl_2$.

Compounds Ib may be obtained by condensing a Grignard agent of formula II

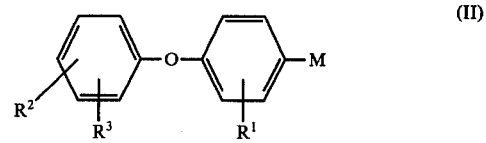

wherein M is magnesium halide and $R^1$, $R^2$ and $R^3$ are as defined above, with a suitable carbonyl compound (III), i.e., a pyridine carboxaldehyde or a pyridyl ketone depending upon whether the $R^4$ is a hydrogen atom or alkyl:

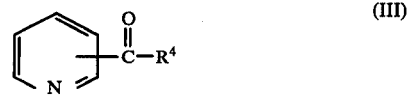

wherein $R^4$ is as defined above, in the presence of an aprotic solvent and under essentially anhydrous conditions, to obtain a corresponding Grignard adduct, which is then hydrolyzed to the corresponding Compound Ib.

The preparation of a compound Ib (process b) is conveniently carried out in the manner, and under the conditions conventionally applied in carrying out the well-known Grignard reactions. Convenient temperatures are those of from about 0° to 70° C., preferably at the reflux temperature of the solvent. Suitable aprotic solvents are ethers, such as tetrahydrofuran and diethyl ether. Magnesium halides include magnesium bromide and iodide; magnesium bromide being preferred as M. It is particularly convenient to prepare a Grignard reagent in which M is a magnesium halide in situ, e.g., by reacting an aryl halide of formula IV;

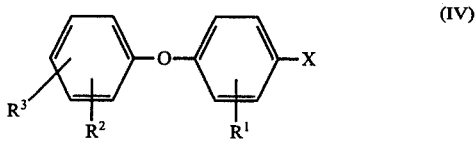

wherein $R^1$, $R^2$ and $R^3$, are as defined above, and X is bromo or iodo, with magnesium metal at temperatures and in a solvent suitable for carrying out process b), under essentially anhydrous conditions. A small amount of solid iodine may be added to aid in initiating the reaction, as is commonly done in preparing Grignard reagents. Avoidance of moisture to achieve essentially anhydrous conditions is exercised, e.g., "dry" solvents and moisture-free apparatus being employed.

The hydrolysis of the resulting adduct may be carried out in the manner conventionally employed in hydrolyzing Grignard adducts, e.g., by treating the Grignard adduct with water, or an aqueous salt, acid or base, e.g., saturated ammonium chloride solution.

The products of the above-described reactions may be recovered and refined in conventional manner, e.g., by crystallization, distillation or chromatographic techniques, such as eluting from a chromatographic column or separating on a silica layer.

Starting materials and reagents used in the above-described reactions, e.g., compounds II and IV are either known and obtained by methods described in the literature, or where not known, may be obtained by methods analogous to those described in the literature. Some of the reactants and starting materials are commercially available.

The above-described reactions may conveniently be represented by the following reaction scheme wherein $R^1$, $R^2$, $R^3$ and $R^4$ and M are as defined above:

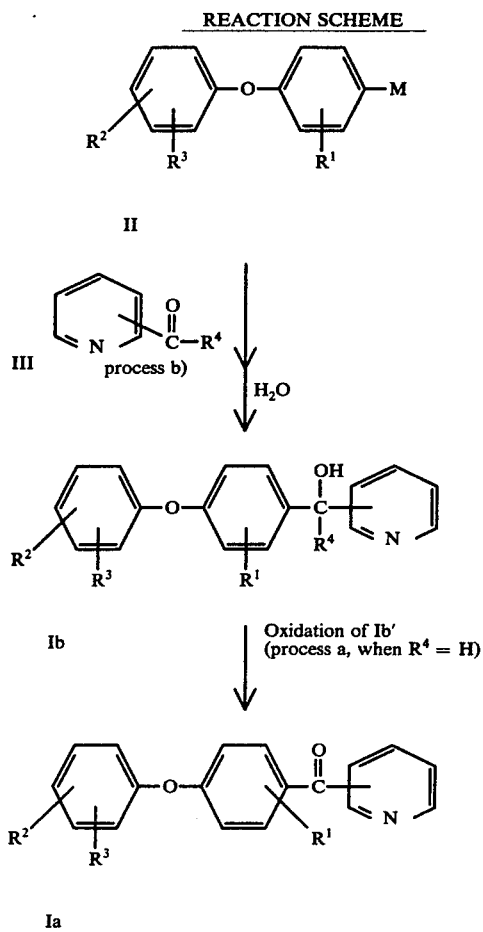

UTILITY STATEMENT

The compounds of formula I are useful because they possess pharmacological activity in animals. In particular, the compounds are useful as hypolipidemic agents in the treatment of lipidemia as indicated by the fall in cholesterol and/or triglyceride levels in male albino Wistar rats weighing 110–130 g. initially. The rats are maintained on drug-free laboratory chow diet for seven days and then divided into groups of 6 to 10 animals. Each group, with the exception of the control, is then given orally 10 to 250 milligrams per kilogram of body weight per diem of the test compound for six days. At the end of this period, the animals are anesthetized with sodium hexobarbital and bled from the carotid arteries. Serum or plasma samples are collected and 1.0 ml. of the serum is added to 9.0 ml. redistilled isopropanol. Two Auto-Analyzer cupsful of a mixture of zeolite-copper hydroxide and Lloydds reagent (Kessler, G., and Lederer, H., 1965, Technicon Symposium, Mediad Inc., New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example from about 20 to 50% of ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

Furthermore, the compounds of formula I may be similarly administered in the form of their non-toxic pharmaceutically acceptable acid addition salts. Such salts possess the same order of activity as the free base, are readily prepared by reacting the free base with an appropriate acid and accordingly are included within the scope of the invention. Representative of such salts are the mineral acid salts, such as the hydrochloride, hydrobromide, sulfate, phosphate and the like and the organic acid salts such as the benzoate, acetate, maleate, fumarate, p-toluenesulfonate, benzenesulfonate and the like.

The hypolipidemic effective dosage of active ingredient employed for the treatment of lipidemia may vary depending on the particular compound employed, the mode of administration and the severity of the condition being treated. However, in general, satisfactory results are obtained when the compounds of formula I are administered at a daily dosage of from about 4 milligrams to about 250 milligrams per kilogram of animal body weight, preferably given in divided doses two to four times a day, or in sustained release form. For most large mammals, the total daily dosage is from about 300 milligrams to about 3000 milligrams. Dosage forms suitable for internal use comprise from about 75 to about 1500 milligrams of the active compound in intimate admixture with a solid or liquid pharmaceutically acceptable carrier. Solid carriers include starch, lactose and kaolin, white liquid carriers include polyethylene glycols and edible oils such as corn, peanut and seasame oils, as are appropriate to the nature of the active ingredient and the particular form of administration desired.

In addition to the above-described utility a particular class of Compounds I, i.e. Compounds Ic of the formula:

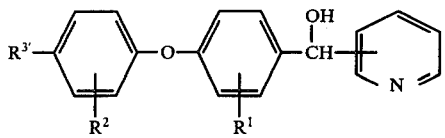

in which $R^1$ and $R^2$ are as defined above, and $R^{3'}$ is alkyl having from 1 to 4 carbon atoms, providing that when $R^2$ and $R^{3'}$ are on adjacent carbon atoms and $R^{3'}$ is a branched alkyl, then $R^2$ is not branched alkyl or branched alkoxy, are also useful as anti-obesity agents in mammals as indicated by the glucose transport test carried out in Male Wistar rats dosed orally with from about 2 to 200 mg/kg of active material, after at least 20 hours of fasting. One hour after receiving the drug, the animal is sacrificed and the upper small intestine is removed and washed with glucose-saline. A 5 cm section of the intestine is everted so that the mucosal surface is on the outside. One end of the segment is tied off and the center of the sac so formed, is filled with oxygen saturated Kreb's bicarbonate buffer. The other end is then closed to form a sac and the sac is incubated in 10 ml. of oxygen saturated bicarbonate buffer for 60 minutes at 37° C. Both the outside and inside solutions contain initially 0.3% of glucose. At the end of the incubation time the glucose content of the outer (mucosal) and the inner (serosal) solution is determined using the standard Autoanalyzer procedure. Similar preparations are prepared simultaneously from animals receiving the vehicle only to serve as controls. The percent inhibition of glucose transport caused by the drug is calculated from the formula $$\% I = 100 - \left( \frac{St - Mt}{Sc - Mc} \times 100 \right)$$

where
I equals inhibition
S equals glucose concentration (mg%) of serosal fluid at the end of an expirment
M equals glucose concentration (mg%) of mucosal fluid at the end of an experiment
c equals control animal
t equals drug treated animal.

Compounds Ic may be administered for treatment of obesity at the same dosages and in the same manner as for the treatment of lipidemia described above, and in the form of their non-toxic acid addition salts when desired.

In the following examples, which are illustrative of the invention, temperatures are in degrees centigrade, and room temperature is 20° to 30° C., unless indicated otherwise.

EXAMPLE 1 p-Phenoxyphenyl Nicotinyl Ketone*

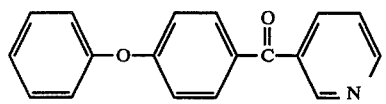

Step (A) α-(p-Phenoxyphenyl)-Nicotinyl Alcohol**

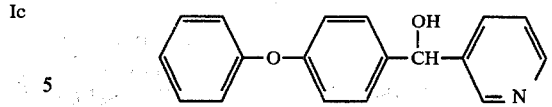

*may also be called p-phenoxyphenyl 3-pyridyl ketone
**may also be called α-(p-phenoxyphenyl)-3-pyridine methanol, or p-phenoxyphenyl 3-pyridyl carbinol.

To 11.5 g. of magnesium metal turnings and a crystal of iodine are added, all at once, 50 ml. of a solution of 116 g. 4-bromodiphenylether in 200 ml. of absolute tetrahydrofuran (THF). After initiating the Grignard reaction, the rest of the THF solution of 4-bromodiphenylether is added dropwise to maintain gentle reflux. The reaction mixture is thereafter refluxed for one hour; cooled and to it is added, dropwise, a solution of 50 g. of 3-pyridinecarboxaldehyde in 100 ml. of absolute THF. The reaction mixture is then stirred for an hour, decomposed with saturated ammonium chloride aqueous solution, and the organic phase, after drying over anhydrous sodium sulfate, is filtered and evaporated under vacuum to dryness. From the residue is crystallized from chloroform, α-(p-phenoxyphenyl)-nicotinyl alcohol, m.p. 129° to 131°.

Step (B) p-Phenoxyphenyl Nicotinyl Ketone

A mixture of 3 g α-(p-phenoxyphenyl)-nicotinyl alcohol and 3 g of activated $MnO_2$ is refluxed in 50 ml dichloromethane for 24 hours. An additional 2 g of activated $MnO_2$ is added and refluxing is continued for an additional 24 hours. Thereafter, the solution is filtered free of $MnO_2$ and evaporated i.v. to dryness. From the residue is crystallized with pentane p-phenoxyphenyl nicotinyl ketone, m.p. 81° to 83°.

EXAMPLE 2

Following the procedure of Example 1, but using in place of the 4-bromodiphenyl ether used in Step A, thereof, an equivalent amount of:
(a) 4-(p-methoxyphenoxy)-bromobenzene;
(b) 4-(p-fluoro-phenoxy)-bromobenzene;
(c) 4-(m-chlorophenoxy)-bromobenzene;
(d) 1-bromo 4-(p-methoxyphenoxy)-3-chlorobenzene;
(e) 1-bromo 4-(p-ethoxyphenoxy)-3-chlorobenzene;
(f) 5-bromo-2-phenoxytoluene;
(g) 4-(p-toloxy)-bromobenzene;
(h) 1-bromo 4-(m-chloro-p-methoxyphenoxy)-3-chlorobenzene;
(i) 4-(3'-5'-di-tert.-butylphenoxy)-bromobenzene;
(j) 4-(p-chlorophenoxy)-bromobenzene; and
(k) 1-bromo 4-phenoxy-3-chlorobenzene.
there is similarly obtained as products of the first and second steps, respectively:
(a) α-[4-(p-methoxyphenoxy)-phenyl]-nicotinyl alcohol, and 4-(p-methoxyphenoxy)-phenyl nicotinyl ketone;
(b) α-[4-(p-fluorophenoxy)-phenyl]-nicotinyl alcohol, and 4-(p-fluorophenoxy)-phenyl nicotinyl ketone;
(c) α-[4-(m-chlorophenoxy)-phenyl]-nicotinyl alcohol, and 4-(m-chlorophenoxy)-phenyl nicotinyl ketone;
(d) α-{[3-chloro-4-(p-methoxyphenoxy)-phenyl]}-nicotinyl alcohol, and [3-chloro-4-(p-methoxyphenoxy)-phenyl] nicotinyl ketone;
(e) α-{[3-chloro-4-(p-ethoxyphenoxy)-phenyl]}-nicotinyl alcohol, and [3-chloro-4-(p-ethoxyphenoxy)-phenyl] nicotinyl ketone;
(f) α-(3-methyl-4-phenoxyphenyl)-nicotinyl alcohol, and 3-methyl-4-phenoxyphenyl nicotinyl ketone;

(g) α-[4-(p-toloxy)phenyl]-nicotinyl alcohol, and 4-(p-toloxy)phenyl nicotinyl ketone;

(h) α-{[3-chloro-4-(m-chloro-p-methoxyphenoxy)-phenyl]}-nicotinyl alcohol, and [3-chloro-4-(m-chloro-p-methoxyphenoxy)-phenyl] nicotinyl ketone;

(i) α-[4-(3′,5′-di-tert.-butylphenoxy)-phenyl]-nicotinyl alcohol, m.p. 161°–164° from pentane; and 4-(3′,5′-di-tert.-butylphenoxy)-phenyl nicotinyl ketone, m.p. 79°–81° from pentane;

(j) α-[4-(p-chlorophenoxy)-phenyl]-nicotinyl alcohol, and 4-(p-chlorophenoxy)-phenyl nicotinyl ketone; and (k) α-(3-chloro-4-phenoxy-phenyl)-nicotinyl alcohol, and 3-chloro-4-phenoxyphenyl nicotinyl ketone.

EXAMPLE 3

Repeating the procedure of Example 1, but replacing the 3-pyridinecarboxaldehyde used therein with an approximately equal amount of (a) 2-pyridinecarboxaldehyde or
(b) 4-pyridinecarboxaldehyde;

there is accordingly obtained as the product of the first step:

(a) p-phenoxyphenyl 2-pyridyl carbinol; and
(b) p-phenoxyphenyl 4-pyridyl carbinol (m.p. 164°–165° from ethanol); respectively, and as the product of the second step:

(a) p-phenoxyphenyl 2-pyridyl ketone (m.p. 47°–49° from methanol); and
(b) p-phenoxyphenyl 4-pyridyl ketone (m.p. 116°–117° from pentane), respectively.

EXAMPLE 4

1-(p-phenoxyphenyl)-1-(3-pyridyl)-ethan-1-ol.

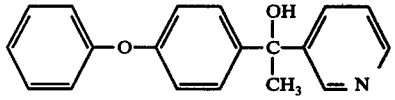

25 ml. of a solution of 25.0 g. 4-bromodiphenylether in 75 ml. tetrahydrofuran is added to 2.5 g. magnesium and, admixed with a small crystal of iodine to initiate the Grignard reaction. Thereafter, the remainder of the solution is added dropwise to maintain gentle reflux. The Grignard solution is then refluxed for 0.5 hours, cooled to 5°–10° and to it is added dropwise 12.1 g. of 3-acetylpyridine. The reaction mixture is then stirred at room temperature for 16 hours, decomposed with saturated aqueous ammonium chloride solution and extracted with ether. The ether extracts are combined and after drying over anhydrous sodium sulfate, filtered and evaporated i.v. to dryness. From the residue is crystallized from pentane/ether, 1-(p-phenoxyphenyl)-1-(3-pyridyl)-ethan-1-ol, m.p. 130°–132°.

EXAMPLE 5

1-(p-phenoxyphenyl)-1-(4-pyridyl)-ethan-1-ol

Repeating the procedure of Example 4, but replacing the 3-acetylpyridine used therein with an equal amount of 4-acetylpyridine, there is accordingly obtained the title product, m.p. 158°–161°.

EXAMPLE 6

1-(p-phenoxyphenyl)-1-(3-pyridyl)-2,2-dimethyl-propan-1-ol.

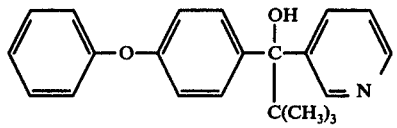

Repeating the procedure of Example 4, but replacing the 3-acetylpyridine used therein with approximately an equivalent amount of t-butyl nicotinyl ketone*, there is accordingly obtained the title product, m.p. 149°–150° C. (from ether).

*may also be called 2,2-dimethyl-1-(3-pyridyl)-propan-1-one or t-butyl 3-pyridyl ketone.

EXAMPLE 7

1-(p-phenoxyphenyl)-1-(4-pyridyl)-2,2-dimethyl-propan-1-ol

Repeating the procedure of Example 6, but replacing the t-butyl nicotinyl ketone used therein with an equal amount of t-butyl 4-pyridyl ketone, there is accordingly obtained the title product, m.p. 134°–135°.

EXAMPLE 8 p-(p-toloxy) phenyl 4-pyridyl carbinol*

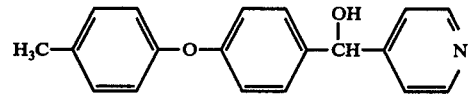

*May also be called 1-[p-(p-toloxy)phenyl]-1-(4-pyridyl)-methanol.

Repeating the procedure of Example 1, but using in place of the 3-pyridinecarboxaldehyde used therein, an approximately equal amount of 4-pyridinecarboxaldehyde, and in place of the 4-bromodiphenyl ether, an approximately equivalent amount of 1-bromo-4(p-toloxy)-benzene; there is accordingly obtained p-(p-toloxy)-phenyl 4-pyridyl carbinol, m.p. 157°–159°. (from ethanol).

Repeating the procedure of this example, but using in place of the 1-bromo-4-(p-toloxy)-benzene, an approximately equivalent amount of 1-bromo-4-(p-tert.-butylphenoxy)-benzene, there is accordingly obtained p-(p-tert.-butylphenoxy)phenyl 4-pyridyl carbinol 178°–9° (from ethanol).**

**May also be called 1-[p-(p-tert.-butylphenoxy)phenyl]-1-(4-pyridyl)-methanol.

EXAMPLE 9

Capsules and tablets containing the ingredients indicated below may be prepared by conventional techniques and are useful in treating lipidemia, particularly hyperlipoproteinemia, in mammals at a dose of one capsule or tablet two to four times per day:

| Ingredient | Weight in Milligrams | | |
| --- | --- | --- | --- |
| | Tablet | Capsule | Capsule |
| p-Phenoxyphenyl nicotinyl ketone | 150 | 150 | 150 |
| Tragacanth | 10 | | |
| Lactose | 97.5 | 100 | |
| Corn Starch | 25 | | |
| Talcum | 15 | | |
| Magnesium Stearate | 2.5 | | |
| Polyethylene Glycol | | | 200 |

| | Weight in Milligrams | | |
|---|---|---|---|
| Ingredient | Tablet | Capsule | Capsule |
| (M.W. 6000) | | | |

EXAMPLE 10

Capsules and tablets containing the ingredients indicated below may be prepared by conventional techniques and are useful in treating lipidemia, particularly hyperlipoproteinemia, and/or obesity in mammals at a dose of one capsule or tablet two to four times per day:

| | Weight in Milligrams | | |
|---|---|---|---|
| Ingredient | Tablet | Capsule | Capsule |
| p-(p-tert.butylphenoxy) phenyl 4-pyridyl carbinol | 150 | 150 | 150 |
| Tragacanth | 10 | | |
| Lactose | 97.5 | 100 | |
| Corn Starch | 25 | | |
| Talcum | 15 | | |
| Magnesium Stearate | 2.5 | | |
| Polyethylene Glycol (M.W. 6000) | | | 200 |

What is claimed is:

1. A compound which is a member of the group consisting of a free organic base of the formula

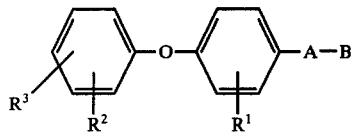

wherein
R¹ is a hydrogen atom, alkyl having from 1 to 4 carbons, fluoro or chloro;
R² is a hydrogen atom, alkyl having from 1 to 4 carbons, alkoxy having from 1 to 4 carbons, fluoro or chloro;
R³ is a hydrogen atom, alkyl having from 1 to 4 carbons, alkoxy having from 1 to 4 carbons, fluoro or chloro;
A is

and
B is an unsubstituted pyridyl radical which may be attached at its 2-, 3- or 4- position, and pharmaceutically acceptable acid addition salts thereof; provided that when R² and R³ are on adjacent carbons they are not both alkyl or alkoxy which are branched.

2. A compound of claim 1 in which R¹ is a hydrogen atom.

3. A compound of claim 2 in which each of R² and R³ is a hydrogen atom.

4. A compound of claim 2 in which at least one of R² and R³ is t.-butyl.

5. The compound of claim 4 which is 4-(3′,5′-di-tert.-butylphenoxy)-phenyl nicotinyl ketone.

6. The compound of claim 1 which is p-phenoxyphenyl 2-pyridyl ketone.

7. The compound of claim 1 which is p-phenoxyphenyl 4-pyridyl ketone.

8. A compound of claim 1 in which B is a 3-pyridyl radical.

9. A compound of claim 1 in which B is a 4-pyridyl radical.

10. A compound of claim 1 in which B is a 2-pyridyl radical.

11. The compound of claim 5 which is p-phenoxyphenyl nicotinyl ketone.

12. A pharmaceutical composition, useful in treating lipidemia, comprising a compound which is a member of the group consisting of a free organic base of the formula

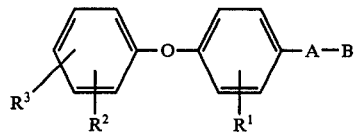

wherein
R¹ is a hydrogen atom, alkyl having from 1 to 4 carbons, fluoro or chloro;
R² is a hydrogen atom, alkyl having from 1 to 4 carbons, alkoxy having from 1 to 4 carbons, fluoro or chloro;
R³ is a hydrogen atom, alkyl having from 1 to 4 carbons, alkoxy having from 1 to 4 carbons, fluoro or chloro;
A is

and
B is an unsubstituted pyridyl radical which may be attached at its 2-, 3- or 4- position, and a pharmaceutically acceptable acid addition salt thereof; provided that when R² and R³ are on adjacent carbons they are not both alkyl or alkoxy which are branched, and a pharmaceutically-acceptable solid carrier.

13. A composition of claim 12 in which B of the compound is a 3-pyridyl radical.

14. A composition of claim 12 in unit dose form in which the compound is present in an amount of from about 75 to 1500 milligrams.

15. A composition of claim 12 in the form of a capsule.

16. The composition of claim 12 in the form of a tablet.

17. A composition of claim 12 in which the compound is p-phenoxyphenyl nicotinyl ketone.

18. A method of obtaining a hypolipidemic effect in a mammal in need of such treatment, which comprises administering orally or parenterally to said mammal a hypolepidemic-effective amount of a compound which is a member of the group consisting of a free organic base of the formula:

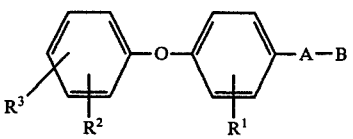

wherein
- R¹ is a hydrogen atom, alkyl having from 1 to 4 carbons, fluoro or chloro;
- R² is a hydrogen atom, alkyl having from 1 to 4 carbons, alkoxy having from 1 to 4 carbons, fluoro or chloro;
- R³ is a hydrogen atom, alkyl having from 1 to 4 carbons, alkoxy having from 1 to 4 carbons, fluoro or chloro;
- A is either

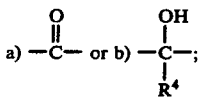

in which
- R⁴ is a hydrogen atom or alkyl having from 1 to 4 carbon atoms, and
- B is an unsubstituted pyridyl radical which may be attached at its 2-, 3- or 4- position, and a pharmaceutically acceptable acid addition salt thereof; provided that when R² and R³ are on adjacent carbons they are not both alkyl or alkoxy which are branched.

19. A method of claim 18 in which B of the compound is a 3-pyridyl radical and R⁴ is a hydrogen atom.

20. A method of claim 18 in which R⁴ of the compound is a hydrogen atom.

21. A method of claim 18 in which the compound is administered in a total daily dosage of from about 300 to 3000 milligrams.

22. A method of claim 18 in which the compound is administered orally.

23. A method of claim 18 in which the compound is administered in admixture with a pharmaceutically acceptable solid carrier.

24. A method of claim 18 in which the compound is p-phenoxyphenyl nicotinyl ketone.

25. The method of claim 18 in which the compound is p-(p-tertiary butylphenoxy)phenyl 4-pyridyl carbinol.

26. A method of claim 18 in which A of the compound is of type a).

27. A method of claim 18 in which A of the compound is of type b).

* * * * *